United States Patent [19]
Cobb et al.

[11] Patent Number: 5,446,185
[45] Date of Patent: Aug. 29, 1995

[54] ALKYLHYDRIDO SILOXANES

[75] Inventors: Vicky S. Cobb, Elsie; Donald E. Mc Vannel, Hemlock; Ann W. Norris; Gary E. Legrow, both of Midland, all of Mich.

[73] Assignee: Dow Corning Corporation, Midland, Mich.

[21] Appl. No.: 338,940

[22] Filed: Nov. 14, 1994

[51] Int. Cl.$^6$ ................................ C07F 7/08
[52] U.S. Cl. .................................... 556/451
[58] Field of Search ......................... 556/451

[56] References Cited

U.S. PATENT DOCUMENTS

| | | | |
|---|---|---|---|
| 5,097,054 | 3/1992 | Yamamoto et al. | 556/451 |
| 5,175,328 | 12/1992 | Okawa et al. | 556/451 |
| 5,232,693 | 8/1993 | Legrow | 424/78 |
| 5,272,243 | 12/1993 | Nakashima et al. | 556/451 X |
| 5,274,156 | 12/1993 | Legrow | 556/445 |

FOREIGN PATENT DOCUMENTS 568318 11/1993 European Pat. Off. .
62-039660 2/1987 Japan .

OTHER PUBLICATIONS

"Silicon Compounds: Register and Review", 5th Edition, Huls America Inc., (1991) pp. 160, 171.

*Primary Examiner*—Paul F. Shaver
*Attorney, Agent, or Firm*—James L. DeCesare

[57] ABSTRACT

Alkylhydrido siloxane fluids including (i) comonomers of the formula $RSi(OSiMe_2H)_3$, (ii) oligomers of the formula $(HMe_2SiO)_2$-$Si(R)$-$O$-$Si(R)$-$(OSiMe_2H)_2$, and (iii) higher molecular weight siloxane species of the formulas $RSi[(OSiMe_2)_xOSiMe_2H]_3$ and $[HMe_2SiO(Me_2SiO)_x]_2SiRORSi[(OSiMe_2)_xOSiMe_2H]_2$, are described in which Me is methyl, and R is a $C_2$ to $C_{18}$ straight-chain or branched-chain alkyl substituent. Methods of making the siloxane comonomers, oligomers, and higher molecular weight species, are also disclosed.

21 Claims, No Drawings

ALKYLHYDRIDO SILOXANES

BACKGROUND OF THE INVENTION

This invention is directed to a family of new alkylhydrido siloxane fluids including comonomers of the formula $RSi(OSiMe_2H)_3$, oligomers of the formula $(HMe_2SiO)_2\text{-}Si(R)\text{-}O\text{-}Si(R)\text{-}(OSiMe_2H)_2$, and higher molecular weight siloxanes of the formula $RSi[(OSiMe_2)_x\text{-}OSiMe_2H]_3$ and $[HMe_2SiO(Me_2SiO)_x]_2SiRORSi[(OSiMe_2)_xOSiMe_2H]_2$; in which Me is methyl; R is a $C_2$ to $C_{18}$ straight-chain or branched-chain alkyl substituent; and x has a value of 1–100.

Although compounds such as methyltris(dimethylsiloxy) silane $CH_3Si(OSiMe_2H)_3$ a and phenyltris (dimethylsiloxy) silane $C_6H_5Si(OSiMe_2H)_3$ are known in the art; that is compounds where R in the formula $RSi(OSiMe_2H)_3$ is either methyl or phenyl, respectively; compounds are not previously known where R is a $C_2$ to $C_{18}$ straight-chain or branched-chain alkyl substituent, as defined above.

SUMMARY OF THE INVENTION

It is therefore an object of the present invention to provide a new family of alkylhydrido siloxane, including their comonomers, oligomers, and higher molecular weight species.

It is also an object of the present invention to prepare such compounds in good yield by hydrolysis of the corresponding alkyltrichlorosilanes with dimethylchlorosilane.

It is a further object of the present invention to equilibrate the new alkylhydrido siloxanes with dialkylcyclosiloxanes, in order to form the hydrido functional siloxanes of higher molecular weight.

These and other objects of the present invention will become more apparent from a consideration of the following detailed description thereof.

DETAILED DESCRIPTION OF THE INVENTION

Siloxanes according to the invention of the formulas $RSi(OSiMe_2H)_3$ and $(HMe_2SiO)_2\text{-}Si(R)\text{-}O\text{-}Si(R)\text{-}(OSiMe_2H)_2$, can be prepared in high yield by hydrolysis of the corresponding chlorosilanes. By hydrolysis is meant simply allowing the chlorosilanes to run into excess water. The reaction is exothermic, owing especially to the heat evolved by dissolution of the hydrogen chloride in water, so that either the reaction mixture must be cooled, or more simply, the halosilanes can be run into ice water.

The reaction is conducted at a temperature of from slightly below 15° C. to 70° C. Preferably, the reaction is conducted at a temperature maintained at least below about 30° C., but most preferably, at a temperature maintained slightly below about 15° C. While temperatures between 30°–70° C. can be employed, lesser amounts of the products may be realized. Typically, the two silanes are added in stoichiometric proportions, which is at least two moles of dimethylchlorosilane for each mole of alkyltrichlorosilane. Other proportions, such as an excess of dimethylchlorosilane can be employed, although no benefits are usually realized from the use of excess amounts. The rate of addition of the silanes to the water should be such that it does not exceed the ability to control the heat evolved during the reaction, and to maintain the temperature within the desired range.

At least an excess amount of water to that mole amount stoichiometrically necessary for complete hydrolysis of the chlorosilane monomers, and to accommodate the HCl generated, should be employed. While the upper limit on the amount of water is not critical, the preferred amount of water is about a nine-fold excess based on $Me_2HSiCl$.

Upon completion of the reaction, the desired siloxane may be easily recovered by any appropriate method. For example, this can be accomplished by draining off the aqueous-HCl bottom layer of the reaction mixture; and washing and neutralizing the siloxane layer. The siloxane layer may be further dried and filtered, if desired. Recovery of the siloxanes can be enhanced by additional steps of solvent stripping and fractional distillation at reduced pressure.

This reaction is shown below in "Scheme 1". In contrast to the present invention as depicted in "Scheme 1", the preparation of $MeSi(OSiMe_2H)_3$ from $MeSi(OMe)_3$ and $Me_2HSiCl$ yields, only 45 percent of the product as shown hereinafter in "Comparison Example V" In further contrast to the invention in "Scheme 1" the preparation of $MeSi(OSiMe_2H)_3$ from $MeSiCl_3$ and $Me_2HSiCl$ yields, only 53 percent of the product as shown in "Comparison Example VI".

Scheme 1

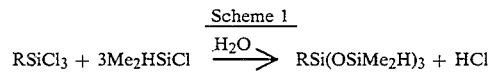

According to "Scheme 1", the alkyl group slows the reactivity of the chlorosilane, so that self-condensation is much slower than when R is methyl (Me) as in $MeSiCl_3$ or $MeSi(OR)_3$. As a result, the yield of $RSi(OSiMe_2H)_3$ is significantly enhanced. Incorporation of an alkyltrichlorosilane makes it possible to eliminate dual waste streams generated when $MeSi(OMe)_3$ and $MesHSiCl$ are employed. In addition, HCl generated in the hydrolysis reaction can be reclaimed.

The amount of $RSi(OSiMe_2H)_3$ obtained in the hydrolysis is dependent upon the temperature at which the reaction is conducted. Where R is n-propyl (Pr), for example, it has been found that when the temperature is maintained slightly below 15° C., 83 percent of the product is $RSi(OSiMe_2H)_3$. At a temperature of 30° C., 79 percent of the product is $RSi(OSiMe_2H)_3$; while at a temperature of 40° C., 47 percent of the product is $RSi(OSiMe_2H)_3$. At higher temperatures, larger amounts of $(HMe_2SiO)_2\text{-}Si(R)\text{-}O\text{-}Si(R)\text{-}(OSiMe_2H)_2$ and the higher molecular weight siloxane species $RSi[(OSiMe_2)_xOSiMe_2H]_3$ and $[HMe_2SiO(Me_2SiO)_x]_2SiRORSi[(OSiMe_2)_xOSiMe_2H]_2$ are formed.

The products $RSi(OSiMe_2H)_3$ and $(HMe_2SiO)_2SiRORSi(OSiMe_2H)_2$ from the hydrolysis in "Scheme 1" above, can be used in the preparation of the higher molecular weight siloxane species. Such higher molecular weight materials are prepared by an acid catalyzed ring opening of cyclic siloxanes such as a dimethylcyclosiloxane, followed by insertion into $RSi(OSiMe_2H)_3$ and $(HMe_2SiO)_2SiRORSi(OSiMe_2H)_2$. Such a process is shown below in "Scheme 2".

Scheme 2

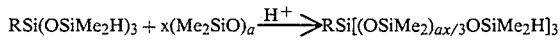

Suitable acid catalysts for use in "Scheme 2" are hydrochloric acid, sulfuric acid, phosphoric acid, oxalic acid, acetic acid, trichloroacetic acid, and trifluoromethane sulfonic acid. The catalyst is present in the reaction medium, usually at a level of 0.01 to 30 percent by weight of the total siloxane. Typically, the acid catalyst can be used within the lower end of this range.

The method according to "Scheme 2" is preferably carried out by creating a mixture comprising the cyclic siloxane $(Me_2SiO)_a$, $RSi(OSiMe_2H)_3$ or $(HMe_2SiO)_2SiRORSi(OSiMe_2H)_2$, and the acid catalyst. The mixture is then heated with agitation at a polymerization reaction temperature, until essentially all of the cyclic siloxane is reacted. The time required will vary depending on the reactants and the reaction conditions.

Polymerization reaction temperatures useful in the method according to "Scheme 2", are typically above the freezing point and below the boiling point of water. Pressures above or below atmospheric pressure may allow operation outside of this range, however. The preferred temperature range is at least 50° C. but less than 95° C.

The polymerization reaction in "Scheme 2" can be stopped at the desired level of conversion of cyclic siloxane, by using methods known in the art. It is preferred to stop the reaction when the largest amount of cyclic siloxane has been reacted, or when the ring-chain equilibrium for the system have been obtained. Reaction times of less than 24 hours, and typically less than 5 hours, are sufficient to achieve the desired level of conversion.

The methods for stopping the reaction typically encompass, neutralization of the catalyst by the addition of an equal, or slightly greater stoichiometric amount of base. Either a strong or a weak base may be used to neutralize the reaction. A suitable weakly basic material for example is sodium bicarbonate. Care must be taken when using a strong base such as sodium, potassium, or ammonium hydroxide, not to over neutralize the reaction, as it may be possible to re-catalyze the reaction. It is preferred to neutralize with sufficient quantities of the base, such that the resulting mixture has a pH of about 7.

Siloxanes of the types shown in "Scheme 1" and in "Scheme 2" including the comonomers, oligomers, and higher molecular weight siloxane species, are useful as intermediates in the preparation of various types of organic modified siloxanes. Thus, these siloxanes have utility as intermediates in the preparation of organosiloxane ethers, which have application in the personal care arena. Reference may be had for example, to U.S. Pat. No. 5,274,156, in which an organosilicon hydride is reacted with an alkenyl ether terminated organic oxyalkylene compound, to produce a mixture of silicone polyethers.

Reference may also be had for example, to U.S. Pat. No. 5,232,693, wherein siloxanes possessing an $\equiv SiH$ functionality in the molecule are reacted with an alkene, to produce certain alkylmethylsiloxanes which are useful in the prevention of dry skin.

In "Scheme 1" or "Scheme 2" above, the group R according to this invention, can be a $C_2$ to $C_{18}$ straight-chain (unbranched) or branched-chain alkyl substituent. Suitable R substituents are for example, ethyl; n-propyl; isopropyl; butyl; 2-methylpropyl; pentyl; 2-methylbutyl; 2,2-dimethylpropyl; hexyl; 2-methylpentyl; 3-methylpentyl; 2,2-dimethylbutyl; 2,3-dimethylbutyl; heptyl; 2-methylhexyl; 3-methylhexyl; 2,2-dimethylpentyl; 2,3-dimethylpentyl; 2,4-dimethylpentyl; 3,3-dimethylpentyl; 3-ethylpentyl; 2,2,3-trimethylbutyl; octyl; nonyl; decyl; undecyl; dodecyl; tridecyl; tetradecyl; pentadecyl; hexadecyl; heptadecyl; and octadecyl.

The cyclic siloxanes most suitable for use in "Scheme 2" are volatile methyl siloxanes of the formula $[(CH_3)_2SiO]_a$, in which "a" has a value of three to six. These volatile methyl siloxanes have boiling points generally less than about 250° C.

Structurally, the volatile methyl siloxanes may be represented as:

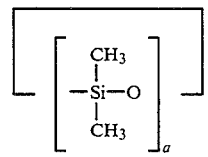

Examples of some suitable cyclic volatile methyl siloxanes are (i) hexamethylcyclotrisiloxane which has a boiling point of 133° C. and the formula $[(Me_2)SiO]_3$; (ii) octamethylcyclotetrasiloxane which has a boiling point of 171° C. and the formula $[(Me_2)SiO]_4$; (iii) decamethylcyclopentasiloxane which has a boiling point of 205° C. and the formula $[(Me_2)SiO]_5$; and (iv) dodecamethylcyclohexasiloxane which has a boiling point of 245° C. and the formula $[(Me_2)SiO]_6$.

This invention is illustrated in more detail in the following examples.

EXAMPLE I

Preparation of $PrSi(OSiMe_2H)_3$
n-propyltris(dimethylsiloxy)silane

A mixture of $PrSiCl_3$ (59.92 g, 0.338 moles) and $Me_2HSiCl$ (95.90 g, 1.014 moles) was added drop-wise to a 3-necked round bottom flask containing ice water (166.0 g, 9.22 moles). The flask was fitted with a thermometer, a mechanical stirrer, and a pressure equalizing addition funnel. The chlorosilanes were added drop-wise through the addition funnel at a rate to maintain a temperature in the flask slightly below 15° C. The solution was vigorously mixed throughout this addition. The solution was stirred for 30 minutes after completion of the chlorosilane addition. An aqueous layer was drawn off, followed by several $NaHCO_3$ washes, and several water washes until neutral to pH paper. The siloxane was dried over $MgSO_4$ overnight and filtered under $N_2$ pressure, yielding a clear, colorless liquid. The final product contained 83% of $PrSi(OSiMe_2H)_3$; 9% of $(HMe_2SiO)_2Si(Pr)-OSi(Pr)(OSiMe_2H)_3$, and 8% of other siloxane impurities. Characterization included Si-29 Nuclear Magnetic Resonance (NMR), Gas Chromatography/Mass Spectrometry (GC/MS), and Gas Chromatography/Flame Ionization Detection (GC/FID).

EXAMPLE II

Example I was repeated, except that room temperature water was used instead of ice water, and the temperature was allowed to rise to 30° C. The final product contained 79% of $PrSi(OSiMe_2H)_3$, 12% of (HMe₂Si- O)$_2$Si(Pr)OSi(Pr)(OSiMe$_2$H)$_2$, and 9% of other siloxane impurities.

EXAMPLE III

Example I was again repeated, except that room temperature water was used instead of ice water, and the temperature was allowed to rise to 40° C. The final product contained 47% of PrSi(OSiMe$_2$H)$_3$, 30% of (HMe$_2$SiO)$_2$Si(Pr)OSi(Pr)(OSiMe$_2$H)$_2$, and 23% of other siloxane impurities.

EXAMPLE IV

Preparation of PrSi[(OSiMe$_2$)$_{3.5}$OSiMe$_2$H]$_3$

A solution of n-propyltris (dimethylsiloxy) silane PrSi(OSiMe$_2$H)$_3$ (18.94 g, 0. 064 moles) prepared in Example I, (Me$_2$SiO)$_4$ cyclosiloxane (49.82 g, 0. 672 moles), and 41 microliters of trifluoromethane sulfonic acid, was heated to 70° C. The flask was fitted with a water cooled condensing column, a magnetic stirrer, and a thermometer. The flask was flushed with N$_2$ prior to heating, followed by N$_2$ positive pressure through the top of the condenser. After heating the flask at 70° C. for four hours, the solution was cooled to room temperature, followed by the addition of NaHCO$_3$ (1.0 g) and diatomaceous earth (Celite) (1.0 g). The mixture was stirred for 4 hours, followed by filtration under N$_2$ pressure, and yielded a clear, colorless liquid. The final average structure determined by Si-29 NMR was (PrSi)$_{1.0}$[(OSiMe$_2$)$_{3.5}$OSiMe$_2$H]$_3$. In that structure, the value "1.0" was plus or minus 0.2; the value "4.0" plus or minus 0.5; and the value "3.0" plus or minus 0.2. Dimethyl cyclic siloxanes were also present in the product.

COMPARISON EXAMPLE V

Preparation of Methyltris(dimethylsiloxy)silane MeSi(OSiMe$_2$H)$_3$ From Methyltrimethoxysilane MeSi(OMe)$_3$ A mixture of methyltrimethoxysilane MeSi(OMe)$_3$ (128.42 g, 0.943 moles) and dimethylchlorosilane Me$_2$HSiCl (267.60 g, 2.828 moles), was added drop-wise to a three-necked round bottom flask containing ice water (166.0 g, 9.22 moles). The flask was fitted with a thermometer, a mechanical stirrer, and a pressure equalizing addition funnel. Addition of the silanes was adjusted to maintain a temperature below 20° C., accompanied with vigorous mixing throughout the addition. The solution was stirred for 30 minutes after completion of the methoxysilane and chlorosilane addition. An aqueous layer was drawn off, followed by several NaHCO$_3$ washes, and several water washes until neutral to pH paper. The siloxane was dried over MgSO$_4$ overnight and filtered under N$_2$ pressure, to yield a clear, colorless liquid. The final product contained only 45% MeSi(OSiMe$_2$H)$_3$, 30% (HMe$_2$SiO)$_2$Si(Me)-OSi(Me)(OSiMe$_2$H)$_2$, and 25% of other siloxane impurities. As in Example I, characterization included Si-29 Nuclear Magnetic Resonance (NMR), Gas Chromatography/Mass Spectrometry (GC/MS), and Gas Chromatography/Flame Ionization Detection (GC/FID).

COMPARISON EXAMPLE VI

Preparation of Methyltris(dimethylsiloxy)silane MeSi(OSiMe$_2$H)$_3$ From MeSiCl$_3$ and Me$_2$HSiCl A mixture of MeSiCl$_3$ (22.29 g, 0.149 moles) and Me$_2$HSiCl (42.37 g, 0.448 moles), was added drop-wise to a three-necked round bottom flask containing ice water (72.54 g, 4.03 moles). The flask was fitted with a thermometer, a magnetic stirrer with stir bar, and a pressure equalizing addition funnel. Addition of the chlorosilanes was adjusted to maintain a temperature below 22° C., accompanied with vigorous mixing throughout the addition. The solution was stirred for 5 minutes after completion of the chlorosilane addition. An aqueous layer was drawn off, followed by several water washes until neutral to pH paper. The siloxane was dried over MgSO$_4$ overnight and filtered to yield a clear, colorless liquid. The final product contained only 53% of MeSi(OSiMe$_2$H)$_3$, 19% of (HMe$_2$SiO)$_2$Si(Me)-OSi(Me)(OSiMe$_2$H)$_2$, and 28% of other siloxane impurities. Characterization included Gas Chromatography/Flame Ionization Detection (GC/FID).

By comparing Examples I and II with "Comparison Example V" and "Comparision Example VI" it can be seen that siloxanes made according to the invention, can be prepared in much higher yield by hydrolysis of an alkylchlorosilane. Thus, in Examples I and II, the yield of PrSi(OSiMe$_2$H)$_3$ was 83% and 79%, respectively. In contrast, and as shown in "Comparison Example V", a preparation of MeSi (OSiMe$_2$H)$_3$ from MeSi(OMe)$_3$ yielded only 45%. In further contrast and as shown in "Comparison Example VI" a preparation of MeSi(OSiMe$_2$H)$_3$ from MeSiCl$_3$ yielded only 53%.

It should be noted that in Examples I to III, the product contained (HMe$_2$SiO)$_2$-Si(R)-O-Si(R)-(OSiMe$_2$H)$_2$, present in amounts respectively of 9%, 12%, and 30%; evidencing that the proportion of the product increased as a function of the temperature used during hydrolysis.

Other variations and modifications may be made in the compounds and methods described herein without departing from the essential features and concepts of the present invention. The forms of the invention described are exemplary only, and are not intended as limitations on the scope of the invention as defined in the appended claims.

That which is claimed is:

1. Compounds selected from the group consisting of (HMe$_2$SiO)$_2$-Si(R)-O-Si(R)-(OSiMe$_2$H)$_2$, RSi[(OSiMe$_2$)$_x$OSiMe$_2$H]$_3$, and [HMe$_2$SiO (Me$_2$SiO)$_{x-2}$SiRORSi[(OSiMe$_2$)$_x$OSiMe$_2$H]$_2$, in which Me is methyl, R is a C$_2$ to C$_{18}$ straight-chain or branched-chain alkyl substituent, and x has a value of 1–100.

2. Compounds according to claim 1 in which R is selected from the group consisting of ethyl; n-propyl; isopropyl; butyl; 2-methylpropyl; pentyl; 2-methylbutyl; 2,2-dimethylpropyl; hexyl; 2-methylpentyl; 3-methylpentyl; 2,2-dimethylbutyl; 2,3-dimethylbutyl; heptyl; 2-methylhexyl; 3-methylhexyl; 2,2-dimethylpentyl; 2,3-dimethylpentyl; 2,4-dimethylpentyl; 3,3-dimethylpentyl; 3-ethylpentyl; 2,2,3-trimethylbutyl; octyl; nonyl; decyl; undecyl; dodecyl; tridecyl; tetradecyl; pentadecyl; hexadecyl; heptadecyl; and octadecyl.

3. Compounds according to claim 1 of the formula (HMe$_2$SiO)$_2$-Si(R)-O-Si(R)-(OSiMe$_2$H)$_2$, in which Me is methyl, and R is a C$_2$ to C$_{18}$ straight-chain or branched-chain alkyl substituent.

4. A compound according to claim 3 in which R is n-propyl.

5. Compounds according to claim 1 of the formula RSi[(OSiMe$_2$)$_x$OSiMe$_2$H]$_3$, in which Me is methyl, R is a C$_2$ to C$_{18}$ straight-chain or branched-chain alkyl substituent, and x has a value of 1–100.

6. A compound according to claim 5 in which R is n-propyl, and x is 4.

7. Compounds according to claim 1 of the formula [HMe$_2$SiO (Me$_2$SiO)$_x$]$_2$SiRORSi[(OSiMe$_2$)$_x$-OSiMe$_2$H]$_2$, in which Me is methyl, R is a C$_2$ to C$_{18}$ straight-chain or branched-chain alkyl substituent, and x has a value of 1-100.

8. A compound according to claim 7 in which R is n-propyl.

9. A method of making compounds of the formula RSi(OSiMe$_2$H)$_3$ and (HMe$_2$SiO)$_2$-Si(R)-O-Si(R)-(OSiMe$_2$H)$_2$ comprising hydrolyzing an alkyltrichlorosilane of the formula RSiCl$_3$ with dimethylchlorosilane, wherein Me is methyl, and R is a C$_2$ to C$_{18}$ straight-chain or branched-chain alkyl substituent.

10. A method according to claim 9 in which the temperature of the hydrolysis reaction is maintained below 70° C.

11. A method according to claim 9 in which the temperature of the hydrolysis reaction is maintained below 30° C.

12. A method according to claim 9 in which the temperature of the hydrolysis reaction is maintained below 15° C.

13. A method according to claim 9 in which there is employed at least two moles of dimethylchlorosilane for each mole of alkyltrichlorosilane.

14. A method of making compounds of the formula RSi[(OSiMe$_2$)$_x$OSiMe$_2$H]$_3$, in which Me is methyls, R is a straight-chain or branched-chain alkyl substituent, and x has a value of 1-100, comprising (i) hydrolyzing an alkyltrichlorosilane with dimethylchlorosilane to form a compound of the formula RSi(OSiMe$_2$H)$_3$, wherein Me is methyl, and R is a straight-chain or branched-chain alkyl substituent; (ii) reacting the compound RSi(OSiMe$_2$H)$_3$ with a dimethylcyclosiloxane in the presence of an acid catalyst; and (iii) allowing the reaction to continue for a time sufficient for the reaction to reach a constant steady state condition.

15. A method according to claim 14 in which R is a C$_2$ to C$_{18}$ straight-chain or branched-chain alkyl substituent.

16. A method according to claim 15 in which R is selected from the group consisting of ethyl; n-propyl; isopropyl; butyl; 2-methylpropyl; pentyl; 2-methylbutyl; 2,2-dimethylpropyl; hexyl; 2-methylpentyl; 3-methylpentyl; 2,2-dimethylbutyl; 2,3-dimethylbutyl; heptyl; 2-methylhexyl; 3-methylhexyl; 2,2-dimethylpentyl; 2,3-dimethylpentyl; 2,4-dimethylpentyl; 3,3-dimethylpentyl; 3-ethylpentyl; 2,2,3-trimethylbutyl; octyl; nonyl; decyl; undecyl; dodecyl; tridecyl; tetradecyl; pentadecyl; hexadecyl; heptadecyl; and octadecyl.

17. Compounds made according to the method defined in claim 14.

18. A method of making compounds of the formula [HMe$_2$SiO(Me$_2$SiO)$_x$]$_2$SiRORSi[(OSiMe$_2$)$_x$-OSiMe$_2$H]$_2$, in which Me is methyl, R is a straight-chain or branched-chain alkyl substituent, and x has a value of 1-100, comprising (i) hydrolyzing an alkyltrichlorosilane with dimethylchlorosilane to form a compound of the formula (HMe$_2$SiO) 2SiRORSi(OSiMe$_2$H)=, wherein Me is methyl, and R is a straight-chain or branched-chain alkyl substituent; (ii) reacting the compound (HMe$_2$SiO)$_2$SiRORSi(OSiMe$_2$H)$_2$ with a dimethylcyclosiloxane in the presence of an acid catalyst; and (iii) allowing the reaction to continue for a time sufficient for the reaction to reach a constant steady state condition.

19. A method according to claim 18 in which R is a C$_2$ to C$_{18}$ straight-chain or branched-chain alkyl substituent.

20. A method according to claim 19 in which R is selected from the group consisting of ethyl; n-propyl; isopropyl; butyl; 2-methylpropyl; pentyl; 2-methylbutyl; 2,2-dimethylpropyl; hexyl; 2-methylpentyl; 3-methylpentyl; 2,2-dimethylbutyl; 2,3-dimethylbutyl; heptyl; 2-methylhexyl; 3-methylhexyl; 2,2-dimethylpentyl; 2,3-dimethylpentyl; 2,4-dimethylpentyl; 3,3-dimethylpentyl; 3-ethylpentyl; 2,2,3-trimethylbutyl; octyl; nonyl; decyl; undecyl; dodecyl; tridecyl; tetradecyl; pentadecyl; hexadecyl; heptadecyl; and octadecyl.

21. Compounds made according to the method defined in claim 18.

* * * * *